United States Patent [19]

Ivri

[11] Patent Number: 5,164,740
[45] Date of Patent: Nov. 17, 1992

[54] HIGH FREQUENCY PRINTING MECHANISM

[76] Inventor: Yehuda Ivri, 68 Silkberry, Irvine, Calif. 92714

[21] Appl. No.: 691,584

[22] Filed: Apr. 24, 1991

[51] Int. Cl.$^5$ ............................................. G01D 15/16
[52] U.S. Cl. ............................. 346/1.1; 346/140 R; 346/139 C
[58] Field of Search ................ 346/75, 140 R, 140 A, 346/139 X, 139 C

[56] References Cited

U.S. PATENT DOCUMENTS

| | | | |
|---|---|---|---|
| 4,240,081 | 12/1980 | Devitt | 346/75 |
| 4,591,883 | 5/1986 | Isayama | 346/140 R |
| 5,063,396 | 11/1991 | Shiokawa et al. | 346/140 R |

OTHER PUBLICATIONS

W. R. Wehl: Ink-Jet Printing: The Present State of the Art for Siemens AG, 1989.

Primary Examiner—Benjamin R. Fuller
Assistant Examiner—Gerald E. Preston
Attorney, Agent, or Firm—Price, Gess & Ubell

[57] ABSTRACT

The present invention provides an ink-jet ejection device which is capable of ejection or ink (including hot melt ink) jet frequencies greater than 50,000 Hz. A cantilevered beam of selected shape is mounted at its base to a piezoelectric element which oscillates the base. The beam is shaped so that its moment of inertia is reduced toward its free end. The element is activated by an oscillating electrical signal the frequency of which is equal to or close to a natural frequency of oscillation of the beam. In the preferred embodiment herein a third or higher modal frequency is utilized. Because of the structural configuration of the cantilevered beam and the selected frequency of oscillation thereof, the tip of the beam oscillates over an amplitude which is significantly greater than the oscillation amplitude of the base. The beam is highly damped and made of low density material so that the tip amplitude is extremely responsive to variations in the base amplitude. The tip of the beam is provided with an aperture which is preferably tapered in cross-section. One opening of the tapered aperture is in fluid communication with a reservoir of ink and the other opening of the aperture is positioned at an appropriate distance from a recording medium such as paper towards which individual droplets of ink from the reservoir are to be propelled. When the tip amplitude is above a predetermined threshold the solid-fluid interaction between the tapered aperture and the ink causes a drop of ink to accelerate through the aperture and be ejected upon each excursion of the tip of the beam toward the printing media.

21 Claims, 4 Drawing Sheets

HIGH FREQUENCY PRINTING MECHANISM

BACKGROUND OF THE INVENTION

1. Field of the Invention

The present invention relates generally to the field of printing mechanisms and more specifically to an extremely high frequency printing mechanism that finds particularly advantageous use in ink-jet-printing, but which may also be advantageous in application to high speed impact printing.

2. Prior Art

In the last several years, ink-jet printers have been gaining in popularity, particularly for use in conventional office applications and also in the areas of desktop publishing and computer-aided design. The popularity of ink-jet printers is attributable to a number of significant advantages as compared to more conventional dot matrix printers. Most significantly, is extremely high print quality and reliability, combined with relatively low noise operation, low manufacturing costs and relatively low maintenance costs. All ink-jet printers eject droplets of ink with a diameter that is usually less than about 100 micrometers, onto a medium such as paper or transparencies. There are various ways of producing ink droplets on demand. Two types of actuators have become established in the market, namely print systems which use piezoelectric transducers and those which use thermoelectric transducers. Such "drop-on-demand" printers are typically no larger than conventional dot-matrix printers and are basically no more expensive to manufacture. The fact that they can print at high speeds and can do so in relative silence, makes them highly desirable for use as a printer in an office environment. Systems are available with, typically, from four to sixty nozzles and resolutions range from about seventy-two drops per inch (dpi) to four hundred dpi. Because of their low power requirements, such ink-jet printers have been used as lap top printers. Up until about 1984, the only "drop-on-demand" ink-jet printers available on the market were piezoelectric printers in which a voltage is supplied to a piezoelectric element. This results in a mechanical displacement, which causes a pressure change, such as in an ink tube, thereby forcing one drop of ink to discharge toward the printing medium, such as paper. In one such prior art piezoelectric ink-jet device, a piezoelectric tube surrounds a flexible tube having ink therein, and terminating in a nozzle from which the drop of ink is to be ejected. An electric pulse is applied to the piezoelectric tube, causing the internal cross-section of the tube to contract or expand. The result is local over-pressure or under-pressure which creates pressure waves which accelerate the ink meniscus and causes a droplet to be ejected from the nozzle. Piezo-diaphragm systems operate on exactly the same principles as piezo-tube ink-jet mechanisms, except that the pressure waves are produced by the flexural movements of a plain piezo-disk on a rigid diaphragm. Still another piezoelectric configuration for ink jet printing applications are print mechanisms with piezo-lamellas. A large plurality of piezo-lamellas are arranged in parallel and extend or contract when subjected to voltage pulses. This movement is also transferred to an ink chamber and an ink droplet is ejected as a result.

More recently, piezo-activated ink-jet mechanisms have come under competition from bubble-jet systems. These systems employ an elongated channel in which there is a heating element behind a nozzle. When a short pulse is applied to the heating element, a small vapor bubble is produced in the ink above the element. The bubble drives ink out of the nozzle with great force and then collapses, cutting off the jet of ink. In contrast to piezo systems in which the defined oscillation of the actuator causes the ink to move, the bubble jet relies solely on capillary action to draw the ink into the nozzle.

One of the critical performance characteristics of all such prior art "drop-on-demand" ink jet systems is the maximum ejection frequency attainable and the ink compatibly with the media (paper) and the channel and nozzle. Solid ink avoids all the problem associated with ink drying up in nozzle. Hot-wax-based solid ink solidifies on contact with the paper and is water resistant, provide maximum contrast and most important does not require special paper and can be used with transparencies. This frequency for piezo tube systems is about 5 kHz. For diaphragm operated piezo systems, it is about 3 kHz. For lamella piezo systems, it is believed to be as high as 10 kHz. However, there is no current system on the market which uses the piezo-lamella concept that is capable of a 10 kHz ejection frequency or ejection of hot-melt-ink. The bubble systems have a maximum ejection frequency of about 4 kHz. Thus, of all of the prior art piezo-electric and bubble ink-jet systems on the market, the maximum ejection frequency is 5 kHz. The ejection frequency is a critical parameter of ink-jet systems because for the same number of nozzles, it determines how quickly a character can be formed, or alternatively, in color ink jet printing applications, it determines how quickly different color combinations can be created, and thus whether or not a color ink-jet printing system can be made that is feasible in terms of print speed. Another critical performance characteristic is resistance to clogging ink channels which can readily occur with long ink channels.

SUMMARY OF THE INVENTION

The present invention provides an entirely new and innovative drop-on-demand printing device that is especially advantageous in ink-jet printing mechanisms. However, the present invention may also have advantageous applications in impact-type printers, as will be seen hereinafter. The principal innovative feature of the present invention is that it is capable of ejecting drops of ink including hot-melt-ink at a much higher ejection frequency than any of the previously described prior art ink-jet printing mechanisms. In fact, the present invention provides an ink-jet ejection device which is capable of ejection frequencies greater than 50,000 Hz. Although the present invention also utilizes a piezoelectric element, in a preferred embodiment, it uses such an element in a totally new and radically different manner. More specifically, in the present invention, a cantilevered beam of a selected shape is mounted at its base to a piezoelectric element. The element is designed to oscillate the base. The beam is shaped so that its moment of inertia is reduced toward its free end and as a result the amplitude is greatly magnified despite high damping. The element is activated by an oscillating electrical signal the frequency of which is equal to or close to a natural frequency of oscillation of the beam. In the preferred embodiment herein a third or higher modal frequency is utilized. Because of the structural configuration of the cantilevered beam and the selected frequency of oscillation thereof, the tip of the beam oscillates over a distance which is significantly greater than the oscillation distance of the base. Thus for example, in a preferred embodiment of the invention described herein this oscillation distance or amplitude at the base is one ten-thousandth of an inch. However because of the shape of the beam and frequency of oscillation selected, the amplitude of oscillation at the tip or free end of the beam is fifteen to twenty times greater than that at the base. The actual ratio of tip amplitude to base amplitude is also a function of the structural damping of the beam. In the preferred embodiment of the invention described herein, the beam is highly damped and made of a low-density material so that the tip amplitude is extremely responsive to variations in the base amplitude. The tip of the beam is provided with an aperture which in the preferred embodiment of the invention described herein is preferrably tapered in cross-section. One opening of the tapered aperture is in fluid communication with a reservoir of ink and the other opening of the aperture is positioned at an appropriate distance from a recording medium such as paper towards which droplets of ink from the reservoir are to be propelled. It has been found that when the amplitude of the free end of the beam, that is, the end having the tapered aperture, is above a predetermined threshold, between the tapered aperture and the ink causes a drop of ink to be accelerated through the aperture and be ejected upon each excursion of the tip of the beam toward the printing media. However, it has also been discovered that by reducing the amplitude of the tip oscillations below the aforementioned preselected threshold, ink droplets will not be ejected. Thus by controlling the amplitude of the oscillations as well as the size and shape of the aperture of the beam and given variations in ink parameters such as viscosity, density and the like, one can readily provide a means for controlled ejection of droplets of ink at an extremely high frequency and lower cost as compared to prior art ink-jet drop-on-demand systems. Furthermore, the relatively short ink path used in the printing device of the invention reduces the likelihood of ink clogging and resulting maintenance.

OBJECTS OF THE INVENTION

It is therefore a principal object of the present invention to provide a printing device capable of operating with a mechanical oscillation frequency in excess of 50,000 Hz.

It is an additional object of the present invention to provide a drop-on-demand ink-jet ejection device capable of ink-droplet ejection frequencies in excess of 50,000 Hz.

It is still an additional object of the present invention to provide a printing element comprising a cantilevered beam having a selected shape for inducing mechanical oscillation of a tip of the beam by mechanical oscillation of the base of the beam at a selected natural frequency.

It is still an additional object of the present invention to provide a high frequency printing device in the form of a cantilevered beam having a base end and a free end, the free end having a reduced moment of inertia compared to the base end having means for imparting mechanical oscillation to the beam at the base end and having a selected shape for imposing an amplified mechanical oscillation at the free end whereby the free end oscillates over a mechanical distance which is sufficient to eject individual drops of ink at a controlled rate in accordance with the oscillation rate of the base end of the beam.

It is still an additional object of the invention to provide a low cost, easily manufactured ink-jet printing device with short ink channels to reduce the likelihood of clogging problems.

BRIEF DESCRIPTION OF THE DRAWINGS

The aforementioned objects and advantages of the present invention as well as additional objects and advantages thereof will be more fully understood hereinafter as a result of a detailed description of a preferred embodiment when taken in conjunction with the following drawings in which.

DETAILED DESCRIPTION OF A PREFERRED EMBODIMENT

Figure 1:
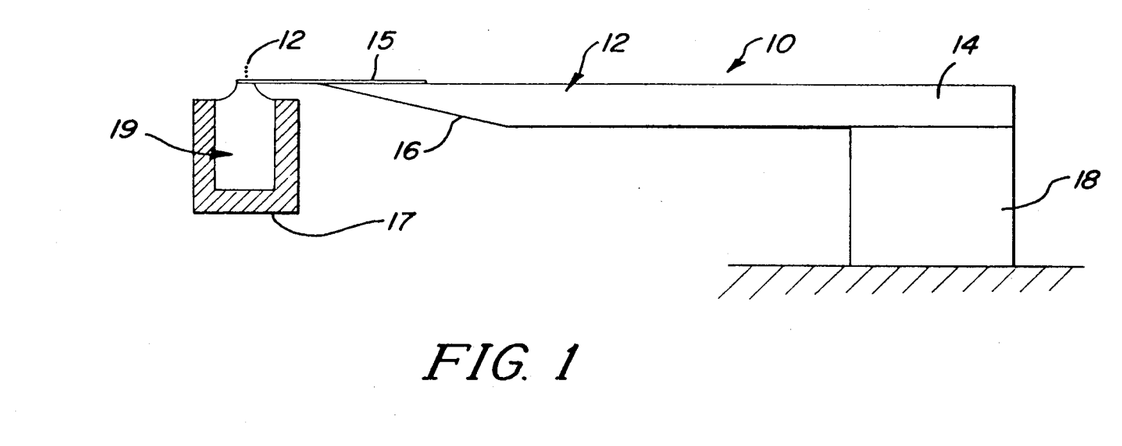
FIG. 1 is a schematic illustration of the printing device of the present invention shown configured for use as a drop-on-demand ink-jet ejection device.

Referring now first to FIG. 1 it will be seen that the printing device 10 of the present invention comprises a cantilevered beam 12 having a base end 14 and a free end 16. The base end 14 of beam 12 is affixed to an oscillator 18 which may for example be made of a piezoelectric material such as EC-28 piezoelectric material supplied by EDD, Inc. in a monolithic corified multilayer configuration. The free end 16 of beam 12 is provided with a relatively planar tip member 15 through which there is an aperture 22. The portion of tip 15 having the aperture is in contact with a source of ink such as ink container 17 which supplies ink 19 to produce an ejection of ink droplets 20.

Figure 2:
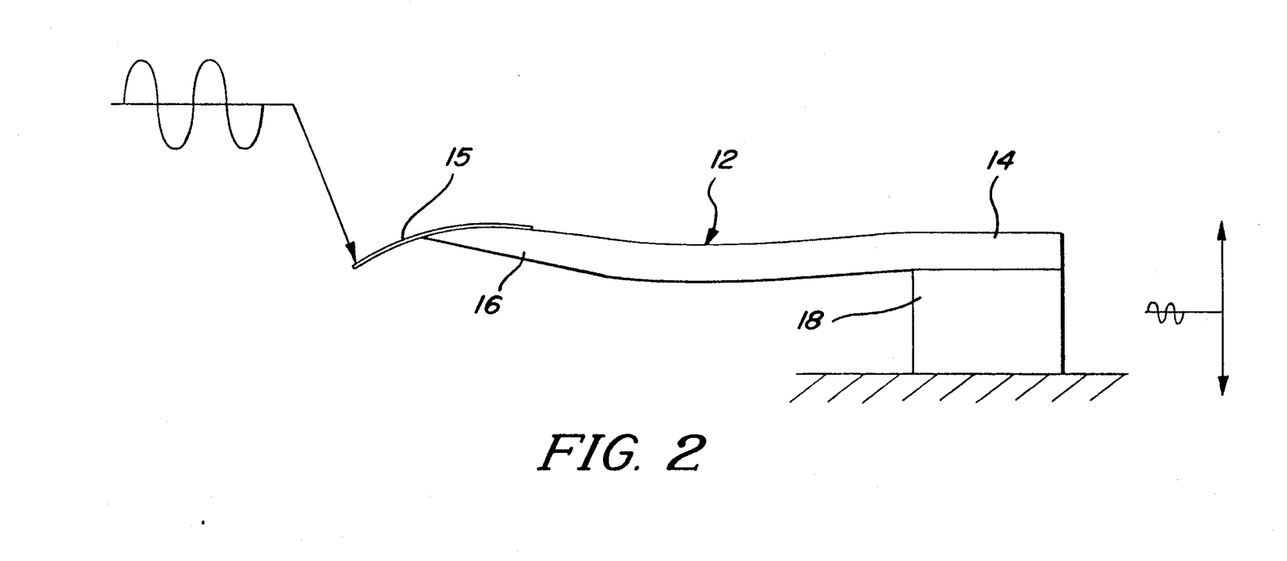
FIG. 2 is a schematic illustration of the cantilevered beam of the present invention shown in its oscillating configuration.

The oscillatory motion of the cantilevered beam 12 is shown in FIG. 2. It will be seen therein, that the base end 14 of the beam 12, by virtue of its intimate contact with the piezoelectric oscillator 18, is caused to oscillate along a vertical axis, as viewed in FIG. 2 with an oscillating characteristic shown in the graph at the rightmost portion of FIG. 2. As also seen in FIG. 2, the free end 16 of beam 12, and particularly the tip element 15 thereof, also oscillates at the same frequency as the base end 14, but with a much larger amplitude as seen in the graph on the leftmost portion of FIG. 2.

Figure 3:
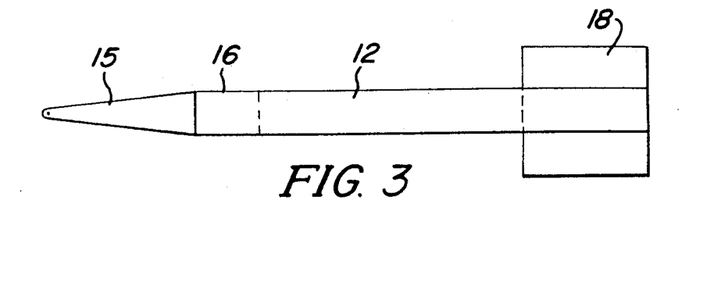
FIG. 3 is a top view of the cantilevered beam of the present invention.
Figure 4:
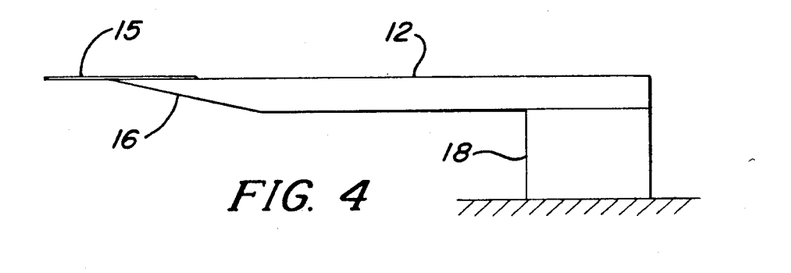
FIG. 4 is a side view of the cantilevered beam of the present invention.
Figure 5:
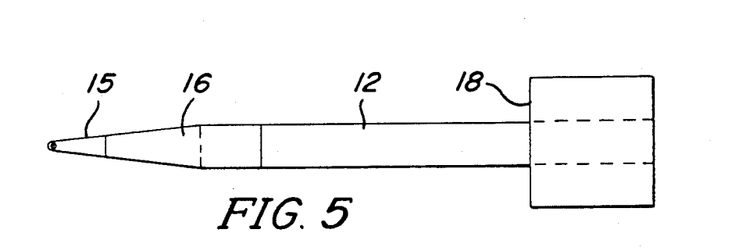
FIG. 5 is a bottom view of the cantilevered beam of the present invention.

The significantly larger oscillation amplitude of the free end of the beam shown in FIG. 2, as compared to the base end thereof, is due primarily to two factors. One is the shape of the cantilevered beam 12 and the other is the frequency of oscillation that is selected for activation of the piezoelectric element 18. More specifically, cantilevered beam 12 is configured so that its moment of inertia along its length is reduced toward the free end. The beam configuration may be understood best by referring to FIGS. 3, 4 and 5 which illustrates a preferred embodiment thereof. From FIGS. 3, 4 and 5 it will be seen that the cantilevered beam 12 is rectangular in shape along a majority of its length, particularly the end thereof denoted as the base end 14. In the preferred embodiment shown therein, the cross-section of the base end is 0.06 inches wide and 0.047 inches high. The overall length of the beam 12, not including the tip element 15, is 0.779 inches. However, the overall beam length is increased by 0.083 inches, which is the degree of overhang of tip element 15 beyond the end of free end 16 of the beam 12. The actual length of the tip element, which partially overlaps the free end 16 of beam 12 is 0.215 inches. The free end 16 of beam 12 is tapered in two planes, while tip element 15 is relatively flat in one plane and tapered in the other to conform to the taper of free end 16. The shape and dimensions of tip element 15 and free end 16 of beam 12 are designed to provide a significantly reduced moment of inertia of the free end of the beam 12, as compared to the base end 14 thereof.

Figure 6:
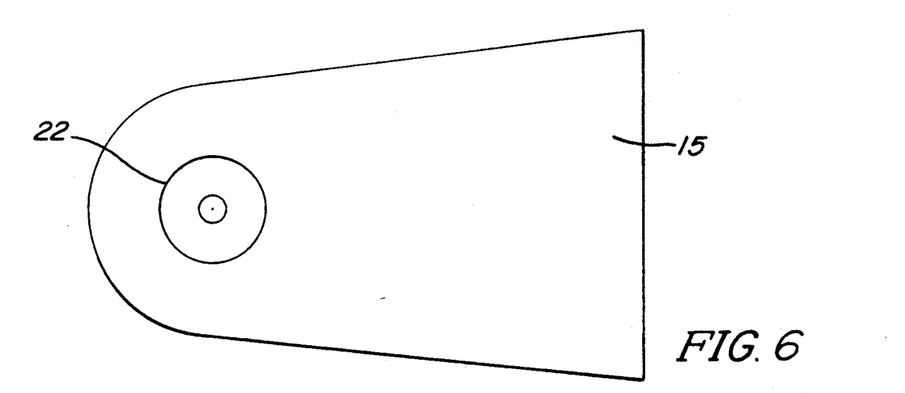
FIG. 6 is an enlarged plan view of the tip portion of the cantilevered beam illustrating that portion of the beam shown in the circle labeled "see FIG. 6" in FIG. 5.
Figure 7:
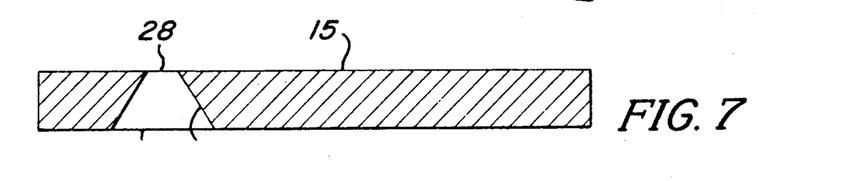
FIG. 7 is a cross-sectional side view of the tip of the cantilevered beam of the present invention showing a preferred aperture shape.

The detailed structure of tip element 15 may be understood best by referring to FIGS. 6 and 7. As seen therein, tip element 15 is provided with an aperture 22, formed by a tapered wall 24, forming a large opening 26 on one side of the tip element 15 and a small opening 28 on the opposite side thereof. The thickness of the tip element 15 in the preferred embodiment shown herein is 0.003 inches. The center of the aperture 22 is positioned at 0.0075 inches from the end of tip element 15 and is circular in shape with large opening 26 having a diameter of 0.005 inches and the small opening 28 thereof having a diameter of 0.0015 inches.

In the preferred embodiment of the invention illustrated herein, the beam 12, including tip element 15, is preferably made of a low-density material such as magnesium-zirconium alloy, with the tip element 15 being separately manufactured in order to simplify the manufacturing process. However, it should be understood that neither the precise shape of beam 12, nor the material thereof is not to be limited by the disclosure of the embodit shown herein. More specifically, it should be understood that tip element 15 can readily be integrated with the remainder of beam 12 to form one elongated structure. Furthermore, the specific shape of such a combined structure would not necessarily be limited to that shown herein, but could be virtually any shape in which the desired reduction in moment of inertia is achieved toward the free end of the beam while providing an aperture of the type shown in FIG. 7 for receiving ink droplets at the large opening 26 thereof and ejecting ink droplets from the small opening 28 thereof. It should also be understood that the specific material, is not to be limiting of the cantilevered beam 12 and that in fact, the beam may be made of a large variety of different materials which may be as suitable for the use intended herein. Other such materials include plastic and composite materials, as well as combinations of metal, plastic and composite materials. The piezoelectric element 18, in the preferred embodiment of the invention shown herein, is of a rectangular block shape having dimensions of 0.19 by 0.19 by 0.125 inches. However, it will be understood that the particular shape of oscillator 18 as well as the use of the piezoelectric materials in general, are not necessarily limiting of the present invention as any suitable oscillator capable of the amplitude and frequency requirement of the present invention may be readily substituted for the element 18 shown herein.

Figure 8:
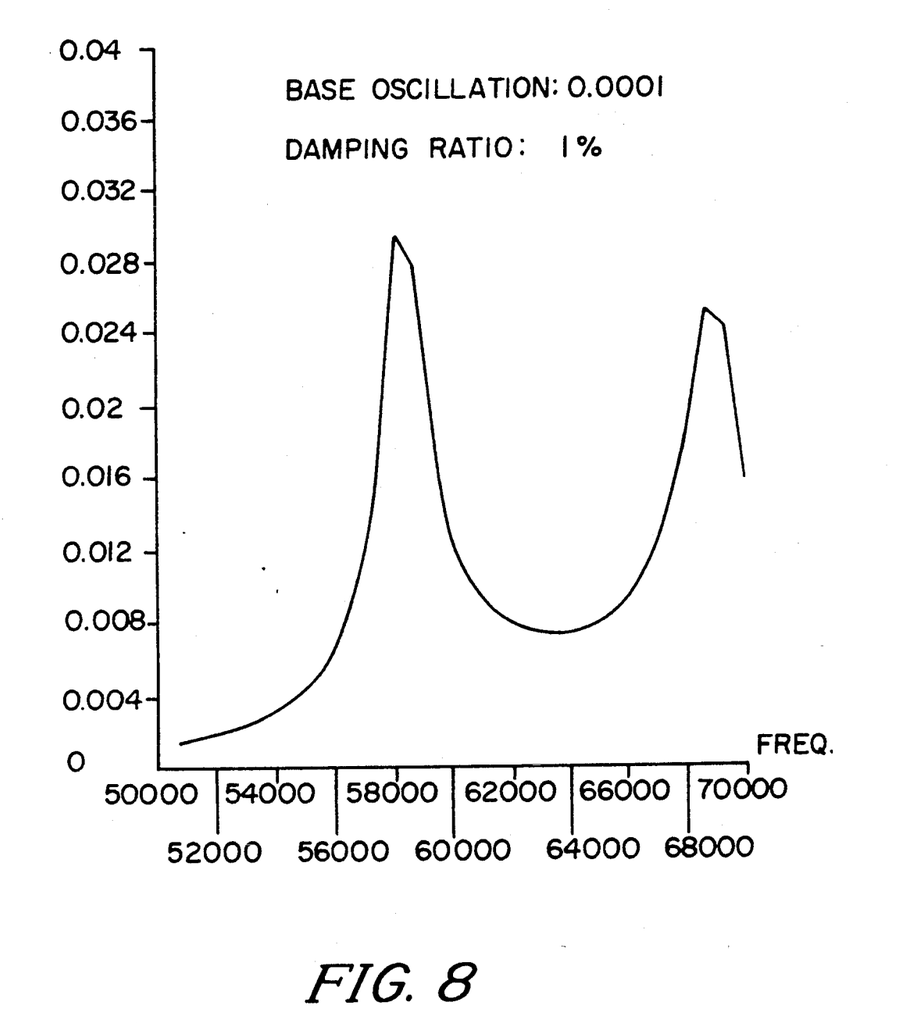
FIG. 8 is a graphical representation of the oscillation characteristics of the beam of FIG. 2 illustrating specifically the amplitude of the third and fourth modal frequencies thereof.

The shape of the beam 12 and in particular the reduction in moment of inertia of the beam between its base end 14 and its free end 16, is selected to provide a significant increase in amplitude of oscillation between the base end and the free end of beam 12 which has been found to occur at particular frequencies of oscillation of the beam 12 and in particular at the third and fourth harmonics of the natural oscillating frequency of the beam. In this regard, FIG. 8 provides a computer-generated graph of the amplitude of oscillation of the free end 16 of beam 12 as a function of frequency, assuming a base oscillation peak amplitude of one ten thousandths of an inch and assuming a damping ratio of 1%. From FIG. 8, it will be seen that the amplitude of oscillation of the free end of beam 12, for the assumed damping ratio of 1%, is approximately is 0.03 inches, that is, 300 times the amplitude of oscillation at the base end 14, at a frequency of 58 kHz which corresponds to the third modal frequency or third harmonic of the natural oscillating frequency of the beam 12. Similarly, the oscillation peak amplitude of the free end of the beam 12, at the fourth modal frequency or fourth harmonic of the natural operating frequency of the beam 12, which occurs at 68 kHz, for the assumed 1% damping ratio is approximately 0.025 inches or 250 times the base oscillation amplitude. Actual measurement of the free end oscillation amplitude using a laser interferometer reveals that the amplitude at the tip is actually 0.002.

Based upon this actual measurement and the fact that the amplitude of the free end oscillation is inversely proportional to the damping ratio and dependent only upon the damping ratio at natural frequencies, the actual damping ratio appears to be approximately 15, that is the average structural damping of the beam 12 is actually 15%. This relatively high damping is a desirable characteristic of the beam structure, because it makes the amplitude of the free end oscillation highly responsive to variations in the amplitude of the base oscillation.

Thus, in the preferred embodiment of the present invention, it is desirable to have a damping factor of at least 10 and to provide an amplitude ratio between the free end and the base end oscillation of also at least 10, depending upon the voltage applied to the oscillator 18 and its mechanical responsiveness thereto.

Figure 9:
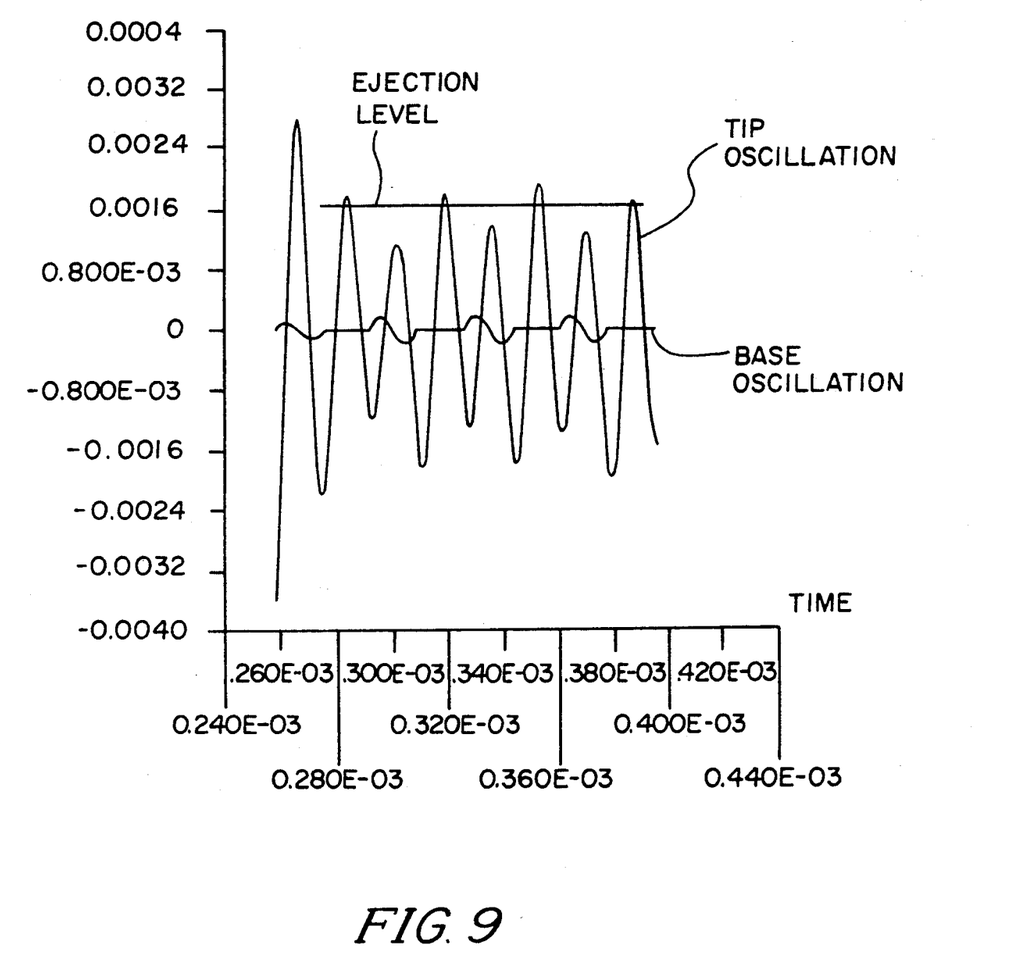
FIG. 9 is a graphical representation of the present invention showing the relative oscillation of the tip compared to the base and the ejection level for ink-jet printing applications.

The cantilevered beam 12 of the present invention is especially useful for ink-jet printing systems, because when the free end of the beam oscillates with an amplitude which exceeds a preselected threshold, ink droplets are ejected from aperture 22 at the frequency of oscillation of oscillator 18. Thus by controlling the amplitude of the base oscillation and thus the amplitude of the free end or tip oscillation so that it is either above or below this threshold ejection level, the ejection of ink droplets may be readily controlled in a manner depicted in FIG. 9. As shown therein, in FIG. 9 the base oscillation amplitude is 0.0001 inches. The frequency of oscillation is approximately 58,000 Hz, which corresponds to the third modal frequency of the beam 12. The ink droplet ejection level, that is the level above which the amplitude of oscillation of the tip or free end 16 of the beam 12 causes ink droplets to be ejected therefrom is approximately 0.0016 inches. As can be seen in FIG. 9, the base oscillation is adjusted so that the tip oscillation varies in amplitude from cycle to cycle, so that it is just above the ejection level upon alternating cycles and below the ejection level therebetween. The actual ejection level threshold, that is the actual oscillation amplitude of the free end of the beam which causes the ejection of ink droplets, depends upon the characteristics of the ink selected, as well as the shape and dimensions of the aperture 22. In the particular preferred embodiment shown herein, the ejection level shown in FIG. 9 is achieved using ink supplied by Sharp, Inc. identified under the model no. JX-735 IFP.

As shown in FIG. 1, the ink 19 continually adheres through solid/fluid surface tension to the large opening 26 of aperture 22. The ink accelerates through the tapered aperture 22 and is ejected one droplet at a time to form droplets 20 shown in FIG. 1. One droplet is ejected each time the amplitude of oscillation of free end 16 at the aperture of tip element 15, exceeds the ejection level threshold. The number of droplets and spacing therebetween, are a function of the frequency of oscillation, which in the preferred embodiment hereof, exceeds 50,000 Hz. It will be understood however, that with selected changes in the shape of the beam 12 and the characteristics of the ink and in the shape and dimensions of aperture 22, the selected frequency of operation, which is preferably a harmonic, such as the third or fourth harmonic, of the natural oscillating frequency of the beam 12, may vary from that shown herein. Nevertheless, based upon the preferred embodiment disclosed herein, it will now be apparent that extremely high frequencies of ink-droplet ejection may be achieved by the present invention and that in fact, ink-droplet ejection frequencies exceeding 50,000 Hz are readily achieved thereby.

It will now be understood that what has been disclosed herein comprises a novel and highly innovative printing device primarily adapted for use in ink-jet printing systems. The invention comprises a cantilevered beam having a base end and a free end, the free end having a lower moment of inertia than the base end. The base end is affixed to a mechanical oscillator for imparting oscillating motion to the base at a selected frequency and of a selected amplitude and an ink supply is in fluid communication with the free end of the beam for supplying droplets of ink to be ejected by the free end upon each oscillation thereof toward a print medium each time the oscillation amplitude exceeds a predetermined threshold amplitude. In a preferred embodiment of the invention disclosed herein the selected frequency of operation is at least a third harmonic or third modal of the natural frequency of the oscillation of the beam. The base end of the beam is oscillated by a piezoelectric material which oscillates in response to an applied oscillating electric voltage.

Because of the shape of the beam and the use of a natural operating frequency or harmonic thereof, the free end oscillation amplitude is at least 10 times greater than the base end oscillation amplitude when the average structural damping of the beam is at least 10. A damping factor of 10 or greater is preferred for use in the present invention in order to make the free end of the beam extremely responsive to variations in the oscillating amplitude in the base end of the beam. In the preferred embodiment of the invention herein disclosed, the selected frequency is greater than 50,000 Hz, thereby providing an ink-droplet ejection frequency characteristic which exceeds all prior art known to the applicant by a significant margin. Such a high ejection frequency makes it feasible to either increase the speed of printing using the present invention or to provide a color printer using a plurality of the printing devices shown herein, each providing ink droplets of a different base color. In such a color printing application, the operating frequency of the combined printing devices is no less than the prior art operating frequency of a black and white ink-jet system. In the preferred embodiment of the invention disclosed herein the free end of the beam is provided with a tip element having a tapered-wall aperture having a large opening for receiving ink and a small opening for ejecting ink droplets.

Those having skill in the art to which the present invention pertains will now, as a result of the applicant's teaching herein, perceive various modifications and additions which may be made to the invention. By way of example, the shapes, dimensions and materials disclosed herein are merely illustrative of a preferred embodiment which has been reduced to practice. However, it will be understood that such shapes, dimensions and materials are not to be considered limiting of the invention which may be readily provided in other shapes, dimensions and materials. Furthermore, it will be understood that the advantageous high frequency operating characteristics of the printing device of the present invention, while having been disclosed for use in ink-jet printing systems, may also find advantageous applications in other forms of printing mechanisms. By way of example, it may be possible to utilize the characteristics of the present invention in an impact printing application wherein the tip or free end of the beam of the present invention may be used as an impact device. Accordingly, all such modifications and additions are deemed to be within the scope of the invention which is to be limited only by the appended claims and their equivalents.

I claim:

1. A device for producing ink droplets on demand and ejecting such droplets toward a print medium, said device comprising:

a cantilevered beam having a base end and a free end, the free end having a lower moment of inertia than the base end, said free end having an aperture therein;

a mechanical oscillator attached to the base end of said beam for imparting oscillating motion thereto at a selected frequency and selected amplitude; and an ink supply in fluid communication with the free end of said beam, said ink being ejected through said aperture in said free end toward said print medium upon said oscillating motion exceeding a predetermined threshold amplitude.

2. The ejection device recited in claim 1 wherein said selected frequency is substantially a natural oscillating frequency of said beam.

3. The ejection device recited in claim 1 wherein said selected frequency is at least substantially the third harmonic of the natural frequency of oscillation of said beam.

4. The ejection device recited in claim 1 wherein said oscillator comprises a piezoelectric material which oscillates in response to an applied oscillating electrical voltage.

5. The ejection device recited in claim 1 wherein said beam is shaped to provide a ratio of free end oscillation amplitude to base end oscillation amplitude which is at least 10 when the average structural damping ratio of said beam is at least 10 percent and said selected frequency is substantially a harmonic of the natural oscillating frequency of said beam.

6. The ejection device recited in claim 1 wherein said selected frequency is greater than 10.

7. The ejection device recited in claim 1 wherein said apertures in the free end of said beam comprises a tapered-wall aperture, said aperture having a first opening for receiving ink from said supply and a second opening from which ink droplets are ejected toward said print medium.

8. The ejection device recited in claim 7 wherein said first opening is larger than said second opening.

9. The ejection device recited in claim 8 wherein the area of said first opening is at least two times the area of said second opening.

10. In an ink-jet printing system, an ink-droplet ejection device comprising:
a vibrating surface having an aperture therein;
an oscillator affixed to said vibratory surface for imparting mechanical oscillations thereto in response to an electrical signal; and
a source of ink for supplying ink droplets to said vibratory surface at the aperture.

11. The ejection device recited in claim 10 wherein said aperture has a tapered cross-section, with an entry opening for receiving ink droplets and an exit opening for ejecting said droplets.

12. The ejection device recited in claim 11 wherein said entry opening is larger than said exit opening.

13. A printing device comprising:
an oscillator;
a vibratory element having a portion affixed to said oscillator and a portion that is free to oscillate in response to the oscillator, the free portion of said element having an aperture therein; and
a supply of printing fluid in contact with the free portion of said vibratory element at said aperture, said writing fluid being ejected through said aperture when the vibratory element is oscillated at a selected frequency and a selected amplitude.

14. The printing device recited in claim 13 wherein said selected frequency is substantially a natural oscillating frequency of said beam.

15. The printing device recited in claim 13 wherein said aperture in said vibratory element comprises a tapered cross-section, with a first opening for receiving said ink droplets and a second opening for ejecting said ink droplets at a rate dependent upon said selected frequency.

16. The printing device recited in claim 15 wherein said first opening is larger than said second opening.

17. The printing device recited in claim 16 wherein said first opening is circular in shape with a diameter of about 0.005 inches, and said second opening is circular in shape with a diameter of about 0.0015 inches.

18. The printing device recited in claim 16 wherein the selected frequency for oscillating said vibratory element is 50 KHz.

19. A method for ejecting ink droplets in an ink jet printing system, the method comprising the steps of:
a. providing a vibratory surface with an aperture therein;
b. oscillating said vibratory surface at a natural oscillating frequency; and
c. supplying ink to said aperture.

20. The method recited in claim 19 wherein said natural oscillating frequency is at least 50 kHz.

21. A device for ejecting fluid droplets comprising:
a vibratory surface having a tapered aperture, said aperture having first and second openings wherein said first opening is larger than said second opening, said first opening being in surface tension contact with said fluid; and
means for vibrating said surface at a selected frequency.

* * * * *

UNITED STATES PATENT AND TRADEMARK OFFICE
CERTIFICATE OF CORRECTION

PATENT NO. : 5,164,740
DATED : November 17, 1992
INVENTOR(S) : Yehuda Ivri

It is certified that error appears in the above-indentified patent and that said Letters Patent is hereby corrected as shown below:

On the title page, item [76]:
In the heading, after "Yehuda Ivri", change "68" to —38—

Signed and Sealed this

Twenty-third Day of November, 1993

Attest:

BRUCE LEHMAN

Attesting Officer     Commissioner of Patents and Trademarks